United States Patent
Vegas Santiago et al.

(10) Patent No.: US 11,380,436 B2
(45) Date of Patent: Jul. 5, 2022

(54) WORKFLOW PREDICTIVE ANALYTICS ENGINE

(71) Applicant: GE Precision Healthcare LLC, Wauwatosa, WI (US)

(72) Inventors: Manuel Vegas Santiago, Madrid (ES); Travis Frosch, Orlando, FL (US); Elodie Weber, Freiburg (DE); Eszter Csernai, Budapest (HU); Erazmus Gerencser, Budapest (HU); Bence Lantos, Budaörs (HU); Andras Kerekes, Budapest (HU); Andras Lanczky, Budapest (HU); Sylvie Jacquot Ingles, Buc (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 238 days.

(21) Appl. No.: 16/691,098

(22) Filed: Nov. 21, 2019

(65) Prior Publication Data

US 2020/0160986 A1    May 21, 2020

Related U.S. Application Data

(63) Continuation-in-part of application No. 16/456,656, filed on Jun. 28, 2019.
(Continued)

(51) Int. Cl.
*G16H 40/20* (2018.01)
*G06N 7/00* (2006.01)
(Continued)

(52) U.S. Cl.
CPC ............. *G16H 40/20* (2018.01); *G06N 7/005* (2013.01); *G06N 20/00* (2019.01); *G16H 10/60* (2018.01)

(58) Field of Classification Search
CPC ........ G16H 40/20; G16H 10/60; G06N 20/00; G06N 7/005
(Continued)

(56) References Cited

U.S. PATENT DOCUMENTS

| 7,693,735 B2 | 4/2010 | Carmi et al. |
| 8,799,009 B2 | 8/2014 | Mellin et al. |

(Continued)

FOREIGN PATENT DOCUMENTS

| CN | 1842788 | 10/2006 |
| CN | 109631935 | 4/2019 |

(Continued)

OTHER PUBLICATIONS

International Searching Authority, "Search Report and Written Opinion," issued in connection with International Patent Application No. PCT/IB2016/050835, dated May 11, 2016, 8 pages.
(Continued)

*Primary Examiner* — Michael Tomaszewski
(74) *Attorney, Agent, or Firm* — Hanley, Flight & Zimmerman, LLC

(57) ABSTRACT

Systems, methods, and apparatus to generate and utilize predictive workflow analytics and inferencing are disclosed and described. An example apparatus includes processor(s) to at least: generate a prediction including a probability of a patient no-show to a scheduled appointment using an artificial intelligence engine including a patient no-show model to predict the probability of the patient no-show based on a combination of healthcare workflow data and non-healthcare information; synchronize the prediction and a schedule including the scheduled appointment; and generate an interactive dashboard including the synchronized prediction and the schedule and at least one of: a) a first option to adjust the schedule to replace the patient based on the probability of (Continued)

the patient no-show orb) a second option to adjust the schedule to move the patient to a different time based on the probability of the patient no-show.

20 Claims, 15 Drawing Sheets

Related U.S. Application Data

(60) Provisional application No. 62/770,548, filed on Nov. 21, 2018.

(51) Int. Cl.
*G06N 20/00* (2019.01)
*G16H 10/60* (2018.01)

(58) Field of Classification Search
USPC .......................................... 705/2–3
See application file for complete search history.

(56) References Cited

U.S. PATENT DOCUMENTS

| | | | |
|---|---|---|---|
| 8,849,689 B1 | 9/2014 | Jagannathan et al. | |
| 9,303,997 B2 | 4/2016 | McGavran et al. | |
| 2005/0256745 A1* | 11/2005 | Dalton | G06Q 40/08 705/3 |
| 2007/0136118 A1 | 6/2007 | Gerlach et al. | |
| 2007/0203761 A1* | 8/2007 | Keen | G16H 50/70 705/5 |
| 2007/0226010 A1 | 9/2007 | Larsen | |
| 2007/0239636 A1* | 10/2007 | Tang | G06N 7/005 706/20 |
| 2009/0164236 A1* | 6/2009 | Gounares | G16H 40/20 705/2 |
| 2010/0106517 A1* | 4/2010 | Kociubinski | G16H 40/20 705/2 |
| 2011/0215933 A1 | 9/2011 | Darling, IV et al. | |
| 2014/0095181 A1 | 4/2014 | Johnson et al. | |
| 2014/0136264 A1 | 5/2014 | Kinsey, II | |
| 2014/0236627 A1 | 8/2014 | Odessky et al. | |
| 2014/0343955 A1* | 11/2014 | Raman | G16H 50/30 705/2 |
| 2014/0365107 A1 | 12/2014 | Dutta et al. | |
| 2015/0242819 A1* | 8/2015 | Moses | G06N 5/04 705/7.19 |
| 2016/0253462 A1* | 9/2016 | Zhong | G06Q 10/04 705/2 |
| 2018/0039742 A1 | 2/2018 | Zhong et al. | |

FOREIGN PATENT DOCUMENTS

| | | | |
|---|---|---|---|
| WO | 2014071023 | 5/2014 | |
| WO | WO-2014071023 A1 * | 5/2014 | ............... G06N 5/04 |
| WO | 2016135587 | 9/2016 | |

OTHER PUBLICATIONS

O'Hare, et al., "The Outcomes of Open-Access Scheduling," Family Practice Management Web site, available at [www.aafp.org/fpm], 2004, 4 pages.
United States Patent and Trademark Office, "Non-Final Office Action," issued in connection with U.S. Appl. No. 15/045,721, dated Dec. 31, 2018, 32 pages.
Michele Samoran, "Outpatient appointment scheduling given individual day-dependent no-show predictions", vol. 240, Issue 1, Jan. 1, 2015, Abstract only, retrieved from https://www.sciencedirect.com/science/article/abs/pii/S0377221714005372?via%3Dihub, on Jun. 28, 2019., 2 pages.
United States Patent and Trademark Office, "Final Office action," issued in connection with U.S. Appl. No. 15/045,721, dated Jun. 26, 2019, 37 pages.
O'Hare "The Outcomes of Open-Access Scheduling," Fam Pract Manag. Feb. 2004;11(2):35-38, retrieved from https://www.aafp.org/fpm/2004/0200/p35.html, on Jul. 16, 2019, 4 pages.

\* cited by examiner

NO-SHOW PROBABILITY FOR PERSONAS AND LOCATION/WEATHER

CHOOSE THE PATIENT AND EXAMINATION LOCATION: 32822, ORLANDO, USA

910
NAME: MARY
SURNAME: POPPINS
AGE: 41 YEARS
EXAMINATION: MAMMO SCREENING
APPOINTMENT AGE: 102 DAYS
DATE/TIME: MONDAY @ 8AM

911
NAME: PABLO
SURNAME: PICASSO
AGE: 63 YEARS
EXAMINATION: KNEE MR
APPOINTMENT AGE: 7 DAYS
DATE/TIME: TUESDAY @ 11AM

912
NAME: CHRISTOPHER
SURNAME: COLOMBUS
AGE: 50 YEARS
EXAMINATION: CHEST CT
APPOINTMENT AGE: 21 DAYS
DATE/TIME: WEDNESDAY @ 1PM

920 FORECAST: SUNNY
921 FORECAST: SUNNY
922 FORECAST: SUNNY

930 NO-SHOW PROBABILITY 56%
931 NO-SHOW PROBABILITY 16%
932 NO-SHOW PROBABILITY 26%

ALTERNATIVE DATE AND TIME FOR MARY POOPINS: 940
MARYPOPPINSDATETIME

FIG. 9

PREDICTED NO-SHOWS FOR NEXT DAYS APPOINTMENTS

1000

CHOOSE THE MODALITY: MR

DECEMBER 2018

| S | M | T | W | T | F | S |
|---|---|---|---|---|---|---|
|   |   |   |   |   |   | 1 |
| 2 | 3 | 4 | 5 | 6 | 7 | 8 |
| 9 | 10 | 11 | 12 | 13 | 14 | 15 |
| 16 | 17 | 18 | 19 | 20 | 21 | 22 |
| 23 | 24 | 25 | 26 | 27 | 28 | 29 |
| 30 | 31 |   |   |   |   |   |

| NAME | AGE | EXAM | MODALITY | DATE | TIME | APPT AGE | NO-SHOW PROB |
|---|---|---|---|---|---|---|---|
| SALVADOR DALI | 71 | LUMBAR SPINE MR | MR | 3/12/18 | 9:00 | 14 | 34% |
| NELSON MANDELA | 70 | BRAIN MR | MR | 4/12/18 | 9:30 | 28 | 30% |
| MARIE CURIE | 62 | ANKLE MR | MR | 5/12/18 | 12:00 | 9 | 28% |
| STEVE JOBS | 41 | ABDOMEN MR | MR | 3/12/18 | 12:30 | 7 | 26% |
| THOMAS EDISON | 75 | SHOULDER MR | MR | 5/12/18 | 12:30 | 10 | 26% |
| TERESA CALCUTA | 85 | PELVIS MR | MR | 4/12/18 | 14:00 | 7 | 25% |
| ROCKY BARBOA | 35 | HEAD MR | MR | 3/12/18 | 8:00 | 7 | 20% |
| MARIA ZAMBRANO | 42 | NECK MR | MR | 5/12/18 | 11:00 | 8 | 18% |
| PABLO PICASSO | 63 | KNEE MR | MR | 4/12/18 | 11:00 | 7 | 16% |

FIG. 10

| PREDICTION REAL | SHOW | NO SHOW | |
|---|---|---|---|
| SHOW | 14905 | FALSE POS.: 24 | 90.8% PRECISION |
| NO SHOW | MISSED: 50 | 238 | |

82.6% RECALL

WORKFLOW PREDICTIVE ANALYTICS ENGINE

CROSS-REFERENCE TO RELATED APPLICATION

This patent arises from U.S. patent application Ser. No. 16/456,656, which was filed on Jun. 28, 2019, and U.S. Provisional Patent Application Ser. No. 62/770,548, which was filed on Nov. 21, 2018. U.S. patent application Ser. No. 16/456,656 is hereby incorporated herein by reference in its entirety. Priority to U.S. patent application Ser. No. 16/456,656 is hereby claimed. U.S. Provisional Patent Application Ser. No. 62/770,548 is hereby incorporated herein by reference in its entirety. Priority to U.S. Provisional Patent Application Ser. No. 62/770,548 is hereby claimed.

FIELD OF THE DISCLOSURE

This disclosure relates generally to improved medical systems and, more particularly, to improved workflow predictive analytics engine systems and associated methods.

BACKGROUND

The statements in this section merely provide background information related to the disclosure and may not constitute prior art.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored can include patient medication orders, medical histories, imaging data, test results, diagnosis information, management information, and/or scheduling information, for example. A wealth of information is available, but the information can be siloed in various separate systems requiring separate access, search, and retrieval. Correlations between healthcare data remain elusive due to technological limitations on the associated systems.

Further, when data is brought together for display, the amount of data can be overwhelming and confusing. Such data overload presents difficulties when trying to display, and competing priorities put a premium in available screen real estate. Existing solutions are deficient in addressing these and other related concerns.

BRIEF DESCRIPTION

Systems, methods, and apparatus to generate and utilize predictive workflow analytics and inferencing are disclosed and described.

Certain examples provide a predictive workflow analytics apparatus. The example apparatus includes a memory including instructions; and at least one processor to execute the instructions to at least: orchestrate a combination of non-healthcare information with healthcare workflow data including patient information and a scheduled appointment for the patient; generate a prediction including a probability of a patient no-show to the scheduled appointment using an artificial intelligence engine in an inferencing mode, the artificial intelligence engine including a patient no-show model to predict the probability of the patient no-show based on the combination of healthcare workflow data and non-healthcare information; synchronize the prediction and a schedule including the scheduled appointment for the patient; and generate an interactive dashboard including the synchronized prediction and the schedule and at least one of: a) a first option to adjust the schedule to replace the patient based on the probability of the patient no-show, b) a second option to adjust the schedule to move the patient to a different time based on the probability of the patient no-show.

Certain examples provide at least one computer-readable storage medium including instructions which, when executed by at least one processor, cause the at least one processor to at least: orchestrate a combination of non-healthcare information with healthcare workflow data including patient information and a scheduled appointment for the patient; generate a prediction including a probability of a patient no-show to the scheduled appointment using an artificial intelligence engine in an inferencing mode, the artificial intelligence engine including a patient no-show model to predict the probability of the patient no-show based on the combination of healthcare workflow data and non-healthcare information; synchronize the prediction and a schedule including the scheduled appointment for the patient; and generate an interactive dashboard including the synchronized prediction and the schedule and at least one of: a) a first option to adjust the schedule to replace the patient based on the probability of the patient no-show, b) a second option to adjust the schedule to move the patient to a different time based on the probability of the patient no-show.

Certain examples provide a method to apply predictive analytics to drive a patient care pathway. The example method includes: orchestrating a combination of non-healthcare information with healthcare workflow data including patient information and a scheduled appointment for the patient; generating a prediction including a probability of a patient no-show to the scheduled appointment using an artificial intelligence engine in an inferencing mode, the artificial intelligence engine including a patient no-show model to predict the probability of the patient no-show based on the combination of healthcare workflow data and non-healthcare information; synchronizing the prediction and a schedule including the scheduled appointment for the patient; and generating an interactive dashboard including the synchronized prediction and the schedule and at least one of: a) a first option to adjust the schedule to replace the patient based on the probability of the patient no-show, b) a second option to adjust the schedule to move the patient to a different time based on the probability of the patient no-show.

BRIEF DESCRIPTION OF DRAWINGS

FIGS. 9-14 depict example interfaces generated by the example systems and methods of FIGS. 1-8.

DETAILED DESCRIPTION

Figure 1:
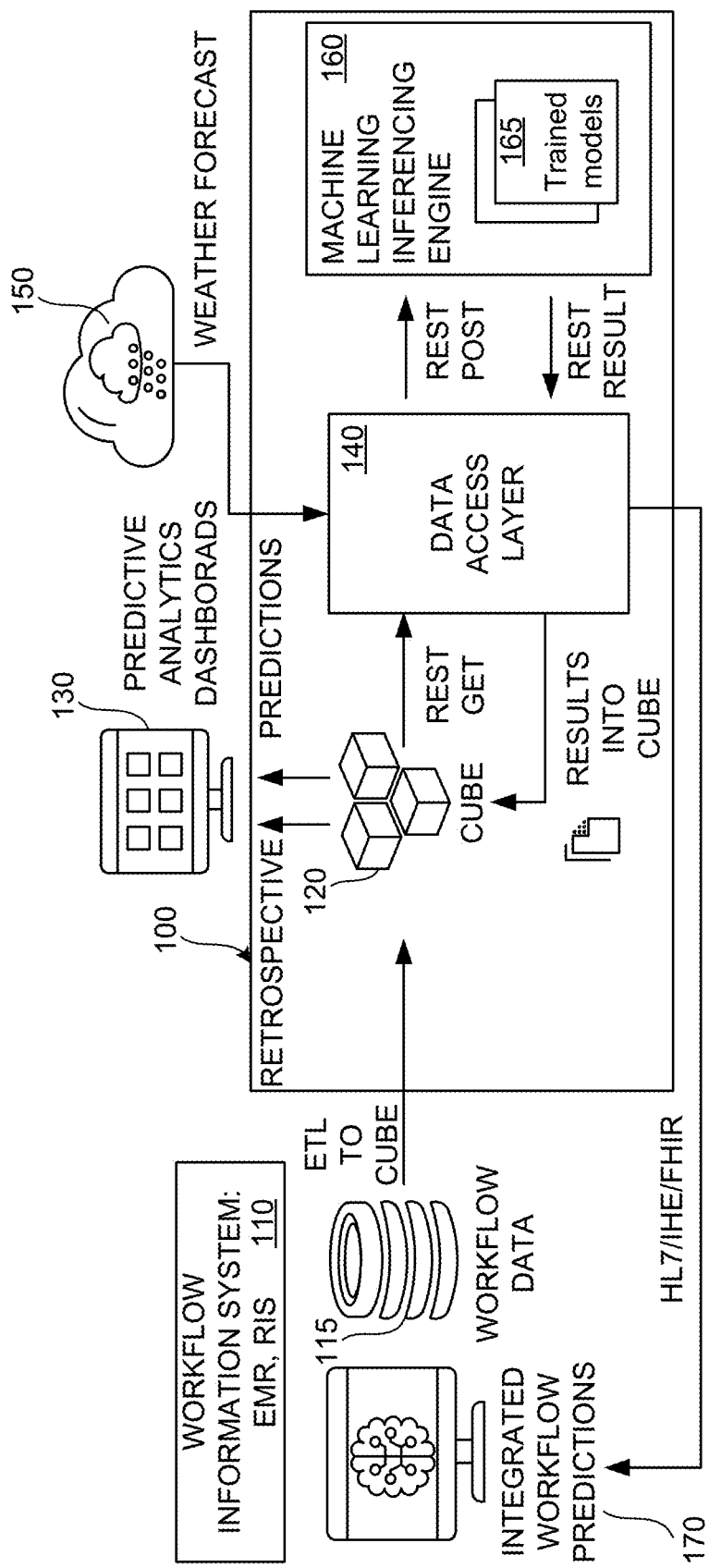
FIG. 1 illustrates an example predictive analytics inferencing architecture.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

In addition, it should be understood that references to "one embodiment" or "an embodiment" of the present disclosure are not intended to be interpreted as excluding the existence of additional embodiments that also incorporate the recited features.

Aspects disclosed and described herein provide systems and associated methods to provide predictive analytics including customer-driven workflow predictions and corresponding responsive actions. For example, predictive analytics disclosed and described herein can be used to avoid breaches in service level agreement (SLA) with respect to reporting, etc., by providing a real-time reporting worklist at a point of decision (e.g., in a radiology information system (RIS), etc.) along with a probability of breach. In another example, patient no-shows can be prevented by identifying examinations having a high probability of no-show and triggering a corrective action such as a reminder, an overbooking analysis, a ride sharing assist, etc., as disclosed and described herein. In another example, patient waiting time can be predicted to improve patient experience and revenue opportunity by computing and announcing an estimated waiting time as disclosed and described herein. In another example, workload and capacity can be managed by planning strategically on a machine and reporting resources needed for each service as disclosed and described herein.

For example, patient no-shows for radiology appointments can be predicted using historical patterns and artificial intelligence processing of patient information (e.g., age, gender, history, etc.), appointment age (e.g., how long since the appointment was made, etc.), date/time of appointment, weather forecast, other historical pattern data, etc. Certain examples leverage artificial intelligence (AI) such as a random forest, artificial neural network (such as a convolutional neural network (CNN), etc.), etc., to provide an integrated prediction and corrective action framework to address likely patient no-show. Patient no shows are costly (e.g., ~$1M loss in yearly opportunity for magnetic resonance imaging exams at a 4% patient no-show rate). A machine learning algorithm and associated model can factor in elements such as weather forecast, location, time, traffic, etc., to predict likely patient no-shows, and a reduced in no-shows increases responsiveness to patient health needs, increased productivity in a healthcare environment, increased revenue, etc., through algorithm-based reconfirmation/replacement strategies, for example.

FIG. 1 illustrates an example predictive analytics inferencing architecture 100. The example apparatus 100 includes and/or interacts with one or more workflow information systems 110, such as an electronic medical record (EMR) system, radiology information system (RIS), picture archiving and communication system (PACS), etc. The information system(s) 110 provide healthcare workflow data 115 to a data store 120, such as an ElastiCube, other data cube, other data store, etc. The workflow data 115 can related to a schedule or workflow of activities involving patients, resources, personnel, etc., for a healthcare facility, for example. The workflow data 115 can be mined using extract, transform, and load (ETL) operations to provide the data 115 to the storage 120, for example. The data storage 120 provides the data to a predictive analytics dashboard 130 as well as a data access layer 140. The dashboard 130 can display prediction(s) from the data 115, for example. The data access layer 140 receives data from the data store 120 (e.g., via a Representational State Transfer (REST) get request, etc.) and combines the data with additional information such as weather forecast information 150 (traffic information, non-healthcare event information, etc.). The data access layer 140 combines the healthcare data 115, such as appointment data, patient data, hospital resource data, etc., with weather forecast information 150 (e.g., looking at a 5-day window around the time of the appointment, etc.) and/or other information such as location, traffic, etc., to form combined, enriched healthcare workflow data, and provides the combined, enriched information (e.g., via a REST post operation, etc.) to a machine learning inferencing engine 160, which includes one or more AI models 165 to process the information and generate a prediction, for example. Results are provided (e.g., via a REST result operation, etc.) back to the data access layer 140 to be conveyed to the data store 120 as well as to the information system(s) 110 as one or more integrated workflow predictions 170.

Thus, data can be aggregated and processed by one more machine learning algorithms implemented using models 165 (e.g., random forest, CNN, etc.) to provide predictive output 170 to the information system(s) 110. The algorithm can change based on a goal of the analysis, degree of probability estimation, accuracy, priority, etc. The example dashboard 130 can provide both predictive and retrospective visualization(s) of information, such as prediction of one or more patient no-shows, etc. In certain examples, a confidence interval can be provided with the predictive estimate. For example, using the prediction of a patient no-show and an associated confidence interval or score (e.g., 90%, 50%, 30%, etc.), the system 110 can decide whether it wants to make an adjustment or change to that patient's appointment (e.g., a reminder, a confirmation, a replacement or substitution of that time slot and associated resource(s), etc.). The confidence interval can be a confidence in the prediction based on available information, and/or the confidence interval can be an indication of confidence that the patient will show up for his/her scheduled appointment, for example.

For example, the prediction can analyze the schedule three days in advance to identify patient(s) associated with a low confidence interval (e.g., <50%), then follow-up with them to confirm whether or not they will be showing up. While rescheduling on the same day is difficult, the schedule can be adjusted up to one day in advance to accommodate a patient who will not or is not likely to attend his/her scheduled appointment. In certain examples, a more urgent patient can be scheduled in place of a patient with a low likelihood of attendance. If a patient is not likely to attend, degradable materials such as nuclear medicine isotopes can be saved, postponed, used instead for another patient, etc., rather than going to waste because the half-life does not allow storage for delayed use.

In certain examples, the output 170 can include a worklist with an indication of confidence/likelihood in attendance/no show, etc. In certain examples, the worklist is generated for follow-up, and patients on the list are prioritized or ranked based on their priority, their likelihood of no show, and available capacity when the list is too long to follow up with everyone.

In certain examples, the worklist can be processed by looking for patients with a same or similar procedure scheduled in the next month to see if a slot can be filled with someone else if the patient currently in that slot does not make his/her appointment. In certain examples, patient address can be compared to clinic location and combined with traffic information to priority patient(s) who can more easily make it to the hospital to fill a time slot.

In certain examples, the data store 120 transforms the data 115 before providing the data to the data access layer 140 and inferencing engine 160. For example, the data store 120 can transform a format of the data 115, can organize/arrange the data 115, etc. Thus, data 115 can be transformed from the RIS to generate a priority list, for example. The model 165 provides output to the data store 120 to be used by the dashboard(s) 130 to present predictive results. The data store 120 can transform the output from the model(s) 165 of the inferencing engine 160 to form a predictive dashboard display 130, for example. Thus, data modeled in the data store 120 (e.g., cleaned, standardized/normalized/transformed, and prepared for output, etc.) can be used to train model(s) 165 and generate prediction(s), for example. The data store 120 can be configured to select a particular subset of the data 115, rather than all the data 115, from the information system(s) 110 that matches certain constraint(s), criterion(-ia), etc., and the data store 120 can organize that data in a certain way for the dashboard(s) 130, model(s) 165, etc.

The model(s) 165 are trained using the prepared data from the data store 120 as further combined with other information such as weather 150, traffic, etc., via the data access layer 140. The data and constraints train, test, and transform the model(s) 165 into particular algorithms customized for the specific data set(s) 115 and observed patient pattern(s) for the particular healthcare environment's system(s) 110. Thus, the model(s) 165 become a customized algorithm or set of algorithms that function for a particular environment, scenario, set of resources, patient population, etc.

In certain examples, the data access layer 140 can send results to the relevant system(s) 110, such as a RIS, PACS, EMR, etc., and appointments can be directly flagged in the RIS scheduling system with a high probability of no-show. Action can be taken to confirm those appointments, cancel or reschedule those appointments, fill in empty time slots with other available patients, etc.

Figure 2:
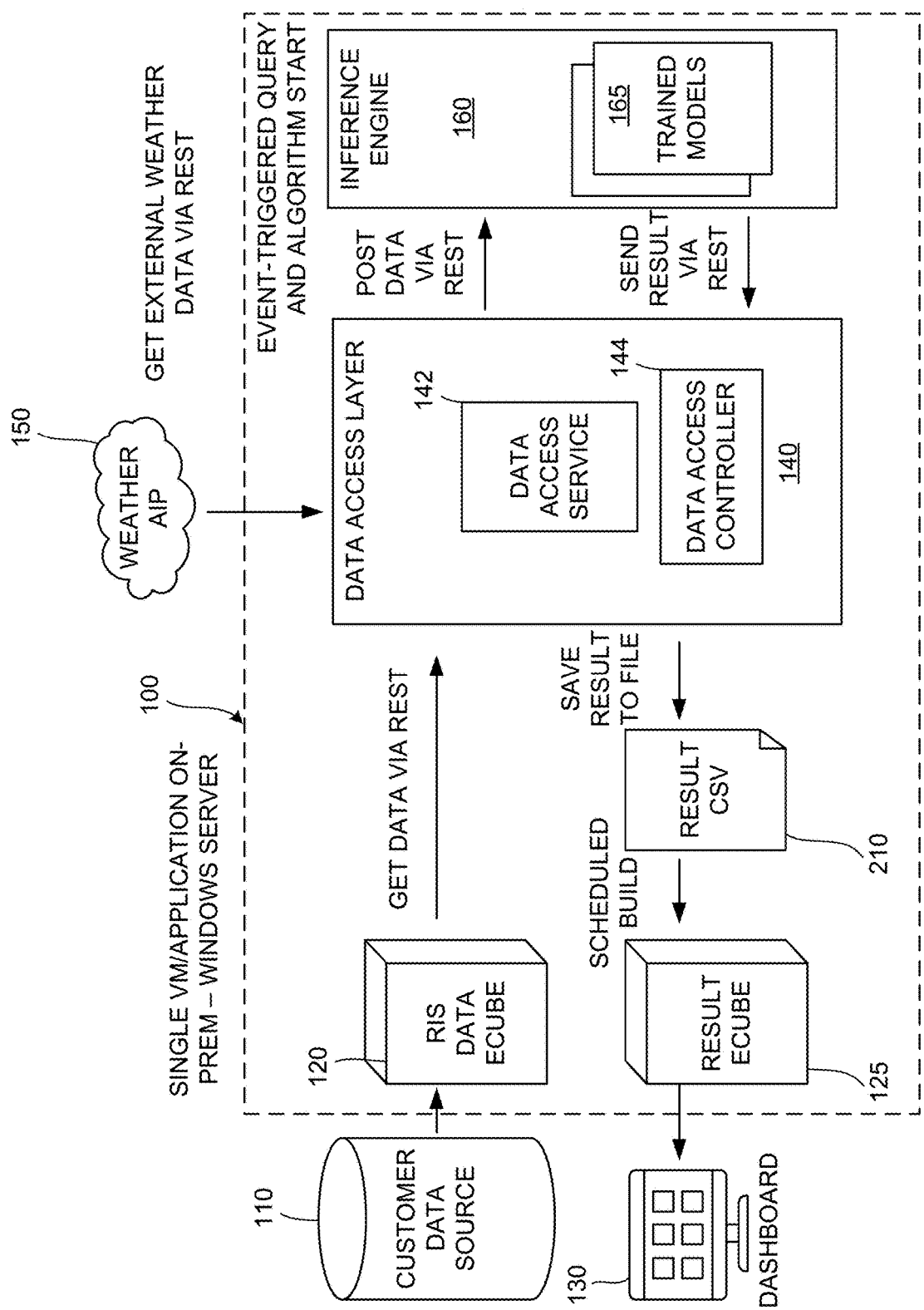
FIG. 2 illustrates a more detailed view of an implementation of the example architecture of FIG. 1.

FIG. 2 illustrates a more detailed view of an implementation of the example architecture 100. In the example of FIG. 2, the architecture 100 is implemented as a virtual machine or appliance running at a healthcare facility (e.g., a hospital, clinic, doctor's office, etc.). In the example implementation of FIG. 2, the data store 120 is divided into a MS data cube 120 and a result cube 125, and the data access layer 140 includes a data access service 142 and a data access controller 144. The data access layer 140 provides a result that is saved in a result file 210, which is provided to the result cube 125. The scheduled build of predictive results from the result file 210 can be used to drive the dashboard 130 interface display(s) and associated action(s).

As shown in the example of FIG. 2, an event at a workflow information system 110 triggers (e.g., based on an appointment or scheduling request, daily schedule generation, etc.) exchange of data and processing of event data, patient data, and other data (e.g., non-health data such as weather, traffic, resources, etc.) to generate an interactive dashboard display and schedule modification. The data cube 120 merges data from multiple sources and enables components of the system 100 to manipulate and query the data as if it was one consolidated data set. Using the cube 120, data from one or more sources 110 at one or more locations can based "mashed" together to represent data in fields in which a value in one field has a corresponding value in another field to enable data in a field to be processed with respect to data in any other field. By allowing data to be analyzed in the context of other data from the same or disparate data source, the cube 120 enables powerful query and analysis of large amounts of data from disparate data source(s) to be processed by the data access layer 140 in real time (or substantially real time given a data retrieval, storage, and/or processing latency, etc.).

In certain examples, the data 115 can be provided to the cube 120 via extract, transform, and load (ETL) operation(s). Using ETL, data 115 can be copied from a source in one context to a destination in another context. Thus, the ETL operation(s) process data retrieved from one or more source(s) 110, cleanse the data to remedy deficiency, inconsistency, etc., from an expected format and/or context, and transform the data into a format/context on which the data access layer 140 can act. In certain examples, ETL operation(s) on the data 115 form the data 115 into a comma separated value (CSV) file and/or other spreadsheet, data file, etc., for retrieval and processing by the data access layer 140.

In certain examples, the data access layer 140 creates a layer of abstraction between the data cube 120 and the inference engine 160. The abstraction of the data access layer 140 allows different logical models to be used with respect to data in the data cube 120 and processing via the inference engine 160 and its model(s) 165, for example. In certain examples, the data access layer 140 can include business logic to tailor queries of data via the data cube 120 and provide an incoming query of the data cube 120 (e.g., data gathered from the cube 120 via a REST get query, etc.) and an outgoing result for the result cube 125. As shown in the example of FIG. 2, the data access layer 140 includes a data access service 142 and a data access controller 144. The data access controller 144 regulates the data access service 142 to get and combine data, process the data, trigger inferencing by the inferencing engine 160, etc. The data access controller 144 can help ensure quality and quantity of data retrieved by the data access service 142 and can help ensure authentication and authorization to retrieve, combine, and process data, for example. For example, the data access controller 144 can control (e.g., via a hypertext transfer protocol (HTTP) request, etc.) the data access service 142 to gather patient and schedule data 115 as well as weather information 150 for a particular time/location to form an execution request for the inference engine 160.

Thus, the data access layer 140 receives data from the data store 120 (e.g., via a REST get request, etc.) and combines the data with additional information such as weather forecast information 150 (traffic information, non-healthcare event information, etc.). The data access layer 140 combines the healthcare data 115, such as appointment data, patient data, hospital resource data, etc., with weather forecast information 150 (e.g., looking at a 5-day window around the time of the appointment, etc.) and/or other information such as location, traffic, etc., and provides the combined information (e.g., via a REST post operation, etc.) to the machine learning inferencing engine 160, which includes one or more AI models 165 to process the information and generate a prediction, for example. The inference engine 160 trains and deploys AI model(s) 165 such as machine learning models (e.g., neural networks, etc.), etc., to process incoming data and determine a likely outcome such as a no-show prediction, etc. The model(s) 165 can be trained, for example, on prior, verified data indicating that certain patient conditions, weather, time/location, etc., result in a patient no-show for an appointment, for example. Results are provided (e.g., via a REST result operation, etc.) back to the data access layer 140 to be conveyed as an output, such as a CVS file 210, etc., to the result data cube 125 as well as to the information system(s) 110 as one or more integrated workflow predictions 170, for example.

Figure 3:
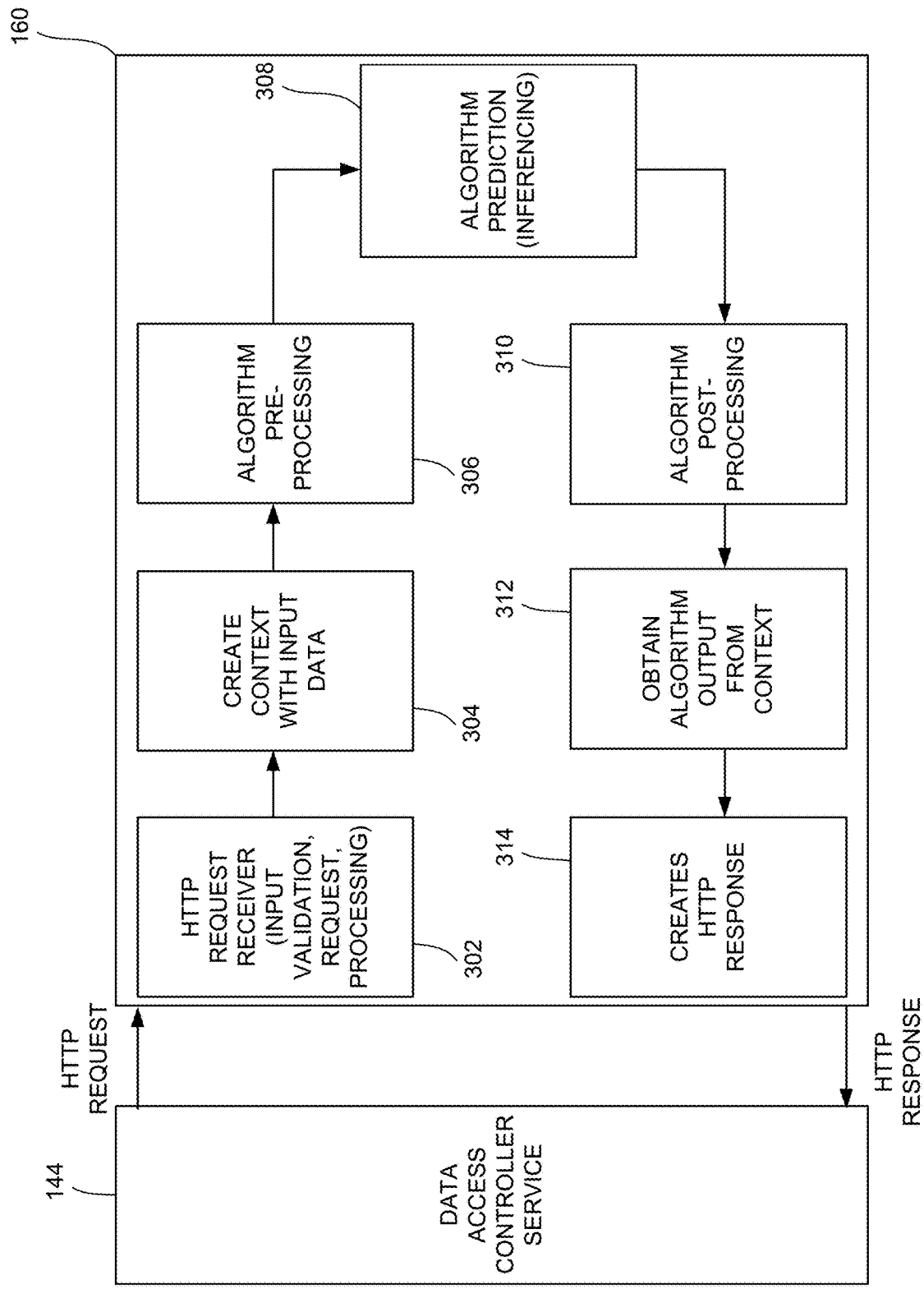
FIG. 3 depicts an example implementation of the inferencing engine of FIGS. 1-2.

FIG. 3 depicts an example implementation of the inferencing engine 160 of FIGS. 1-2. As shown in the example of FIG. 3, the inferencing engine 160 can be implemented as a container or virtual machine including a plurality of elements or actions 302-314. For example, the inferencing engine of FIG. 3 includes an HTTP request receiver 302 to perform input validation, request processing, etc. The receiver 302 provides the processed data to a context creator 304, which creates a patient/schedule context using the input data. For example, context such as reason for exam, patient condition, location, time, etc., can be associated with the data. The data with context is then provided to a preprocessing algorithm 306, which prepares the data for processing by the AI model(s) 165 to generate a prediction (e.g., a no-show prediction, an SLA breach prediction, a wait time prediction, a workload prediction, etc.). The prediction is then output to an algorithm postprocessor 310 to take the model 165 result(s) and formulate the result(s) for use in display, records, schedule adjustment, communication, other output, etc. The post-processed result(s) are provided an output contextualizer 312 to provide context (e.g., patient context, schedule context, etc.) to the output. The contextualized output is then provided to a response generator 314 to create a response (e.g., an HTTP response, etc.) to be send to the data access controller service 144 of the data access layer 140, for example.

Thus, the inferencing engine 160 is a framework component that provides connectivity and expansibility to accommodate one or more algorithm models 165, pre- and/or post-processing, and scalability to scale up algorithm(s) to support a workflow across one or more hospital departments, teams, etc. The engine 160 can scale predictive analytics in the model(s) 165 for a number of sources, number of recipients, intended audience/environment, etc. In certain examples, a variety of models 165 can be plugged in to the engine 160 depending on target goal/objective, patient population, healthcare environment, etc., the model(s) 165 are incorporated into the engine 160 transparent to the user and/or healthcare system 110. The engine 160 provides a framework to accept the algorithm model 165 and adapt that model 165 to a real world system 110, for example.

For example, the model 165 is unable to connect to other parts of the system 110, and the engine 160 connects the model 165 to the system 100, allows it to be changed, enables it to be used, etc. The framework of the engine 160 anchors the model 165 and establishes connections with other parts of the system 100. For example, data from which the prediction is made comes from the database/cubes 120, forwarded via the data management service of the access layer 140, and the inferencing engine 160 exposes an HTTP endpoint, for example, to receive the data and process the data to help ensure quality, format, etc. The pre-processed data is then forwarded to the model 165. Code executed by the engine 160 before the model 165 and after the model 165 preprocesses data going into the model 165 and post-processes data coming out of the model 165 to be used by the system 100 after the model 165.

In certain examples, the model 165 is generated as a random forest model. Random forests or random decision forests are an ensemble learning method for classification, regression and other tasks that operate by constructing a multitude of decision trees at training time and outputting a class that is a mode of included classes (classification) or a mean prediction (regression) of the individual trees, for example. Random decision forests correct for decision trees' habit of overfitting to their training set, for example. That is, decision tree structures can be used in machine learning, but, when the tree grows deep, the tree can learn irregular patterns, resulting in low bias but high variance as the decision tree overfits its training data set. Random forests average multiple deep decision trees, trained on different parts of the same training set, to reduce variance. The reduction in variance can come at the expense of a small increase in the bias and some loss of interpretability, but, generally, greatly boosts performance in the final model. Random forests can be used to rank importance of variables in a regression or classification problem, such as a likelihood or probability of patient no-shows, in a natural way.

In certain examples, random forest predictors can lead to a dissimilarity measure among observations. A random forest dissimilarity measure can also be defined between unlabeled data. A random forest dissimilarity can be used to process mixed variable types because it is invariant to monotonic transformations of the input variables and is robust to outlying observations. The random forest dissimilarity accommodates a large number of semi-continuous variables due to its intrinsic variable selection. For example, a random forest dissimilarity can be used to weigh a contribution of each available variable according to how dependent the variable is on other variables. The random forest dissimilarity can be used to identify a set of patient(s) among a group of scheduled patients who are likely to not show for their scheduled appointment based on past history, weather, traffic, etc.

Machine learning techniques, whether random forests, deep learning networks, and/or other experiential/observational learning system, can be used to locate an object in an image, understand speech and convert speech into text, establish correlations and/or prediction of an event such as a patient no-show, improve the relevance of search engine results, etc., for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Figure 4:
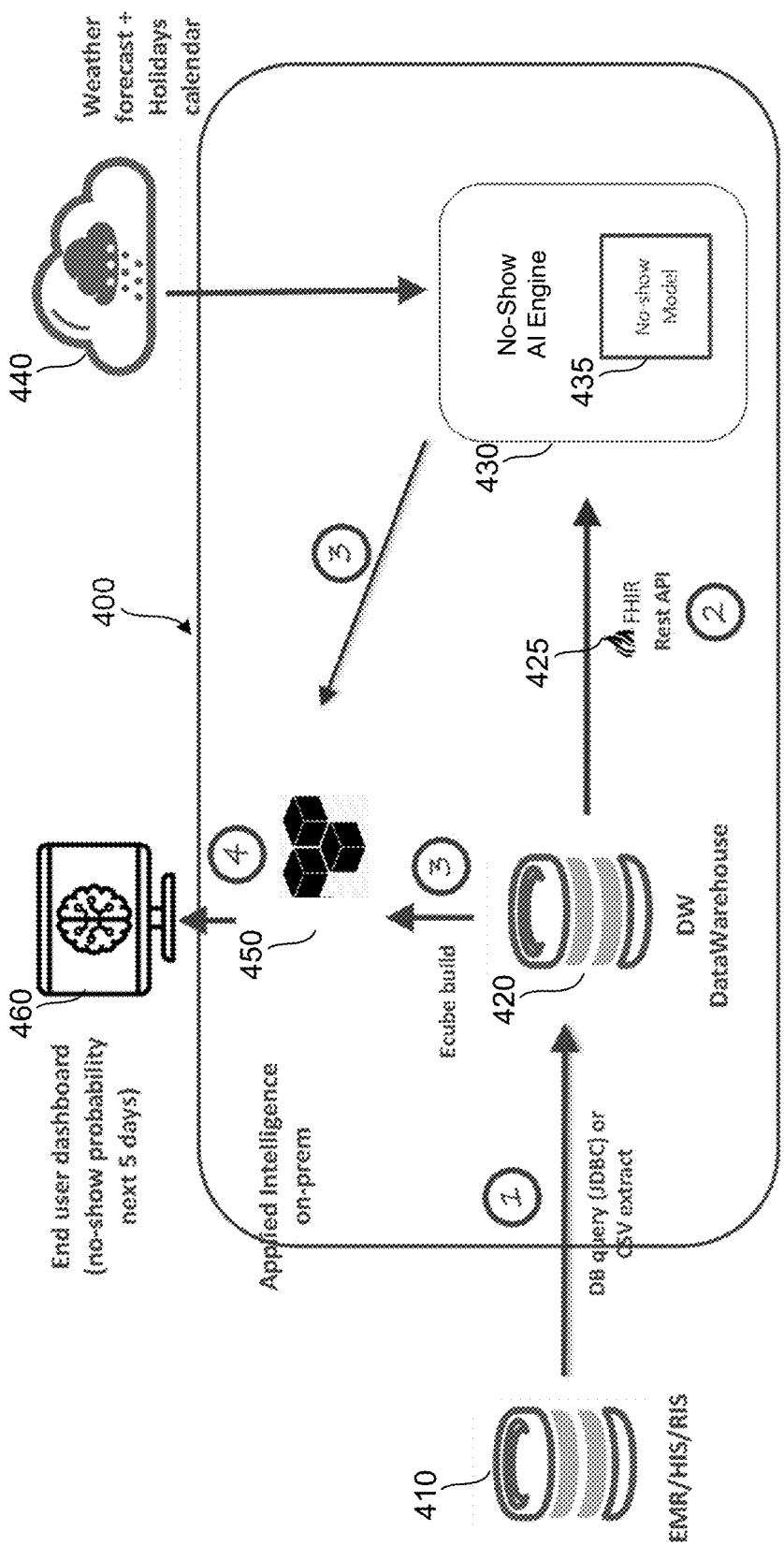
FIG. 4 depicts another example predictive analytics inferencing architecture.

FIG. 4 depicts an alternate example predictive analytics inferencing architecture 400 to identify/predict patient no-shows, similar to but different from the example architecture 100 of FIG. 1. While the example of FIG. 4 is directed to predicting and/or otherwise identifying patient no-shows (e.g., for scheduled exams, procedures, other appointments, etc.), the example architecture 400 can be leveraged for other analytics, modeling, and/or reactive prediction such as patient wait time, diagnosis, imaging insights, predictive reporting, etc. The example architecture 400 includes a query or data extract 1 (e.g., a Java Database Connectivity (JDBC) query, CSV extract, etc.) from a data source 410, such as an EMR, HIS, RIS, etc., to be stored in a data warehouse (DW) 420. An application programming interface (API) 425, such as a REST API, etc., can be used to provide data 2 from the data warehouse 420 to an AI engine 430 (e.g., a no-show AI engine 430), which includes one or more AI model constructs 435 (e.g., a no-show model, etc.). In certain examples, the API 425 can be implemented as a Fast Healthcare Interoperability Resources (FHIR) API 425 defining FHIR resources as a set of operations or interactions with respect to resources in which resources are managed by type. FHIR allows data from the data warehouse 420 to be exposed for training of the model 435, inferencing using the model 435, etc. The data warehouse 420 combines data from a plurality of sources including the information system 410 and other clinical and/or non-clinical data sources such as one or more social, weather, traffic, holiday/calendar, and/or other data stream, dispatch, query, etc. For example, a cloud-based data source 440 can provide weather forecast, holiday calendar, and/or other information to be combined with patient health data, schedule information, capacity, resources, etc., at the AI engine 430. Data is provided to the AI engine 430 and used to generate a predictive output (e.g., a prediction of patient no-show) with the model 435, for example. The FHIR API 425 enables output of the engine 430 to be integrated with other hospital/clinical systems, for example.

Information from the data warehouse 420 and the AI engine 430 can be provided 3 to a data store 450, such as a Sisense ElastiCube analytics database and/or other analytics/relational data store. The data store 450 organizes data for analysis and querying, such as to generate 4 a dashboard 460 for end user interaction. For example, a predictive exam count, no-show probability by time of day, appointment type, patient type, etc., can be displayed for viewing, interaction, etc., via the dashboard 460. The dashboard 460 can also be a retrospective dashboard recapping a number of exams and a corresponding number of patient no-shows, a breakdown of patient no-show by age and/or other demographic, etc. Interaction with the dashboard 460 can drive improvement of the model 435, other adjustment of the engine 430, action at a clinical system 410 (e.g., a change in schedule, duration, resource allocation, etc.), etc.

Figure 5:
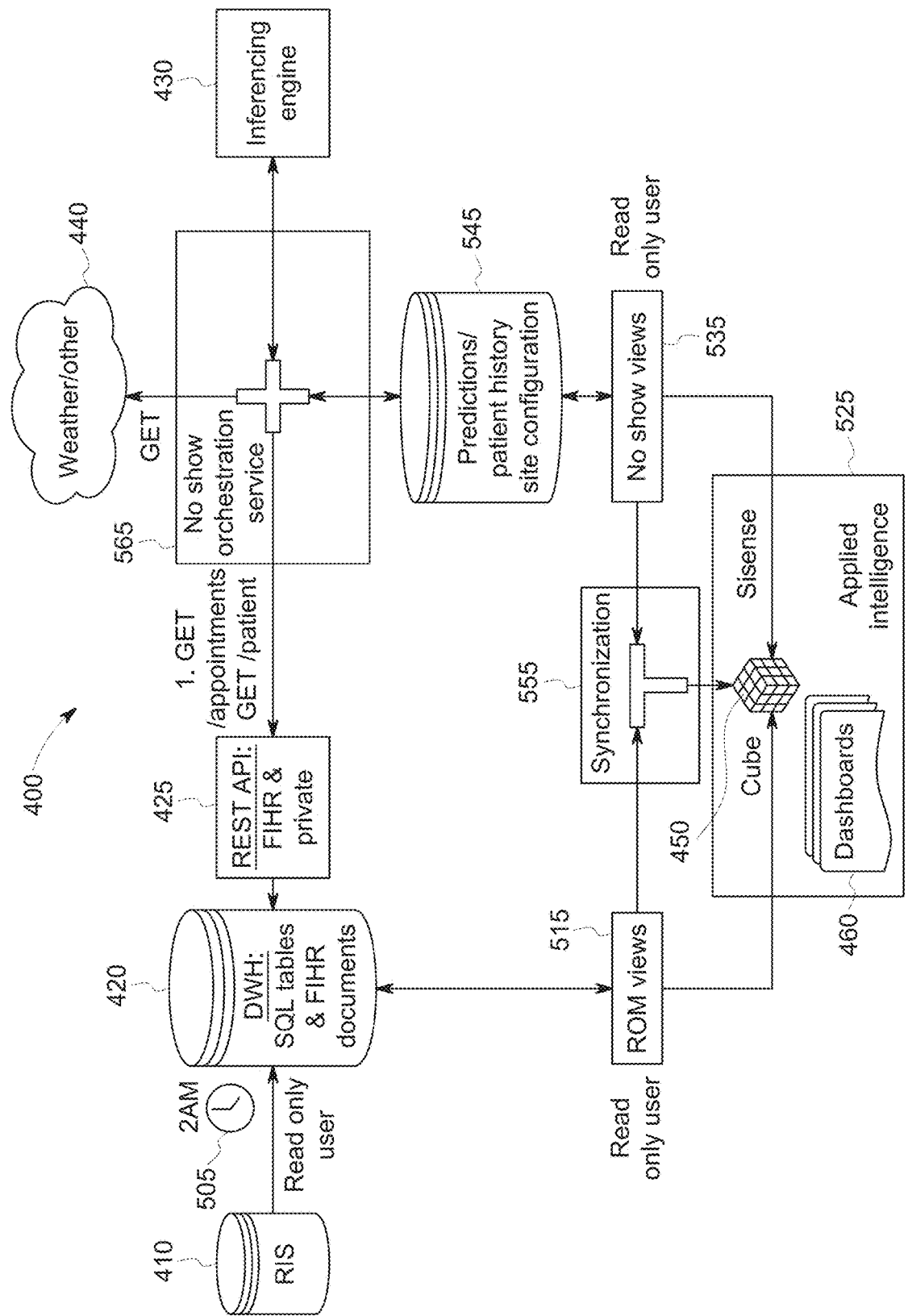
FIG. 5 illustrates a more detailed view of an implementation of the example architecture of FIG. 4.

FIG. 5 depicts the example architecture 400 in operation to predict patient no-shows and generate a dashboard display. As shown in the example of FIG. 5, a query 505 can be scheduled of the data source 410, such as a RIS, etc., to provide an update, download, dispatch, etc., to the data warehouse 420 (e.g., a 2:00 AM read-only data dump from the RSI 410 to the data warehouse 420, etc.). The data warehouse 420 organizes the data according to one or more structured query language (SQL) tables, FHIR documents, etc., for further query, retrieval, analysis, processing, association, etc. Information 515 (e.g., read only memory exchange, etc.) can be exchanged between the data warehouse 420 and an applied intelligence engine 525 including the data cube(s) 450, one or more dashboard 460, etc. The data cube 450 can be used to combine, synchronize, and orchestrate information for predictive output, dashboard 460 generation, dashboard 460 display, etc. Additionally, information 535 regarding no-shows, etc., can provided from a data store 545 of predictions, patient history, site configuration information, etc. Schedule data and no-show data can be synchronized using a synchronizer 555 to provide information to the applied intelligence engine 525 to be organized, correlated, and stored in the data cube 450, used to generate the dashboard(s) 460, etc. The synchronizer 555 combines a retrospective views of data with a prediction to generate content for the dashboard 460, etc.

As shown in the example of FIG. 5, an orchestration service 565 serves as an intermediary between the data store 545, the external weather/holiday/traffic data source 440, and the engine 430 (e.g., in inferencing, rather than training, mode) to correlate weather, holiday, traffic, and/or other information with patient no-show prediction, site information, etc., to drive prediction of patient no-shows, etc. The orchestration service 565 can leverage the FHIR API 425 to get and/or post appointments for a particular location, patients involved in the appointments, etc. Output can be provided via the API 425 in a bi-lateral link with the RIS 410 and/or other scheduling system. As such, when an available appointment slot is retrieved, provided, displayed, suggested, etc., a probability of patient no-show associated with that appointment slot is also determined and provided. A schedule of appointments can be filled and/or otherwise adjusted according to a probability of patient no-show in one or more scheduled appointment slots, for example.

Figure 6:
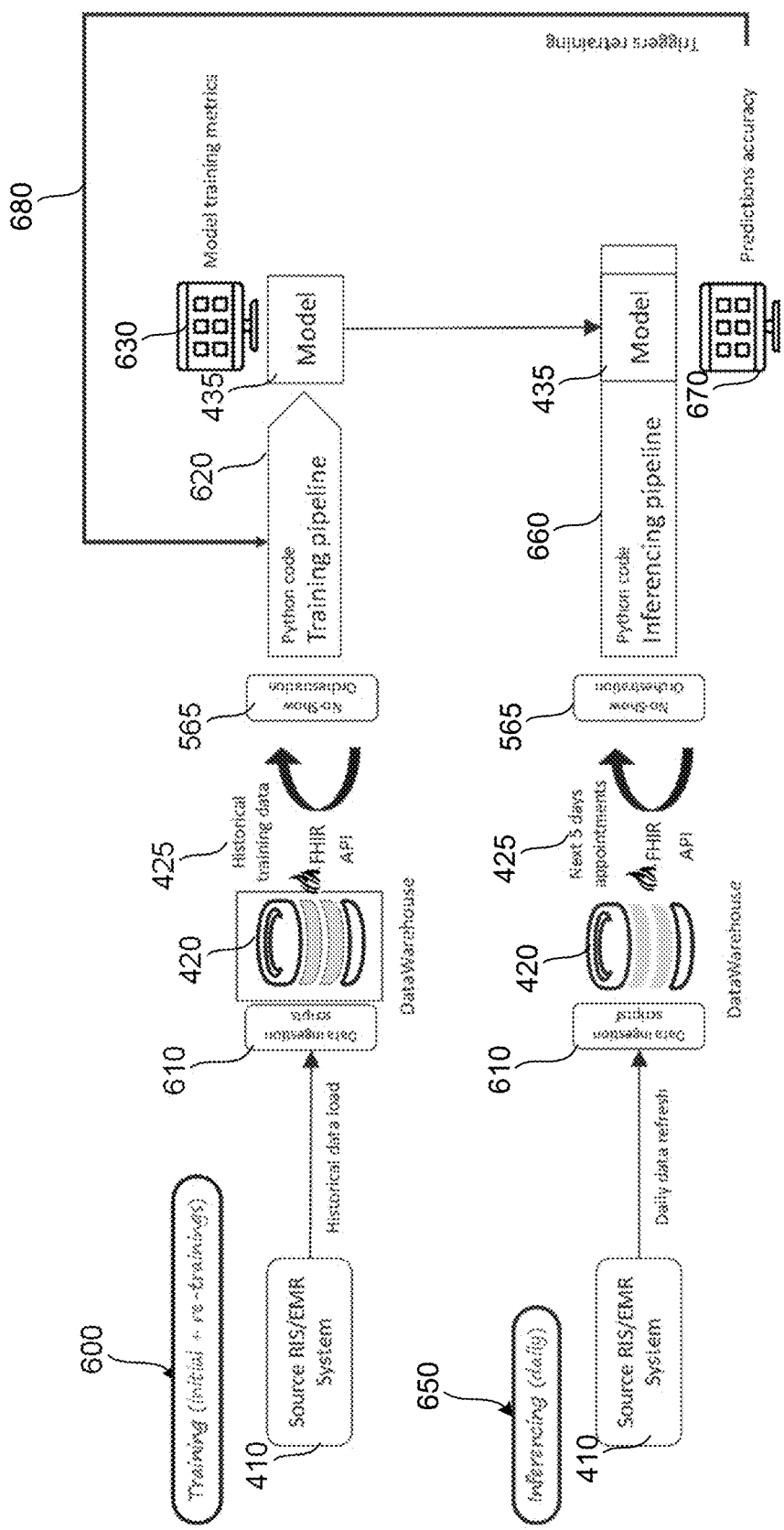
FIG. 6 shows example training and testing processes and associated pipelines for the AI model of FIGS. 1-5.

FIGS. 6A-6B show example pipelines 600, 650 for training 600 and inferencing 650 of the AI engine 430 and its model 435. The example training pipeline 600 is used for initial training and re-training after a certain time period has passed, a certain level of feedback has been received, a certain error threshold in predictive no-show percentage/rate/etc. has been exceed, etc. The example training pipeline 600 processes a historical data set from a source system 410 (e.g., RIS, EMR, HIS, PACS, CVIS, etc.). The historical data is loaded into the data warehouse 420 using one or more data ingestion scripts 610 that can extract, transform, format, organize, query, etc., the data from the source system 410 for storage, correlation, other analysis, etc., in the data warehouse 420. The FHIR API 425 can be used to extract historical training data from the data warehouse 420 to be processed by the no-show orchestration service 565 to provide input to the model 435 via a training pipeline 620. Data in the training pipeline 620 is provided as input to train the model 435. One or more model training metrics 630 can be generated analyzed to determine when the model 435 has been trained and is ready for deployment, use, etc., versus adjusting model 435 weights, parameters, etc., to continue the training 600.

Once training is complete, the model 435 can be deployed and/or otherwise activated in an inferencing mode 650. In certain examples, inferencing 650 can be performed daily on a daily update of data from the source system 410. The source system 410 provides a daily refresh to the data ingestion script(s) 610, which store the information in the data warehouse 420. The FHIOR API 425 provides information (e.g., a next five days of appointments, a next day's appointments, a next week's appointments, etc.) to the no-show orchestration service 565 to prepare the information for submission via an inferencing pipeline 660 for input to the AI model 435. The model 435 provides a prediction 670 (e.g., a prediction of patient no-show, etc.), which can be evaluated for accuracy. An accuracy of prediction 670 can be evaluated over time and can trigger retraining 680 if the accuracy of prediction 670 is less than a threshold, outside a range, and/or otherwise fails to satisfy a retraining criterion, for example.

Figure 7:
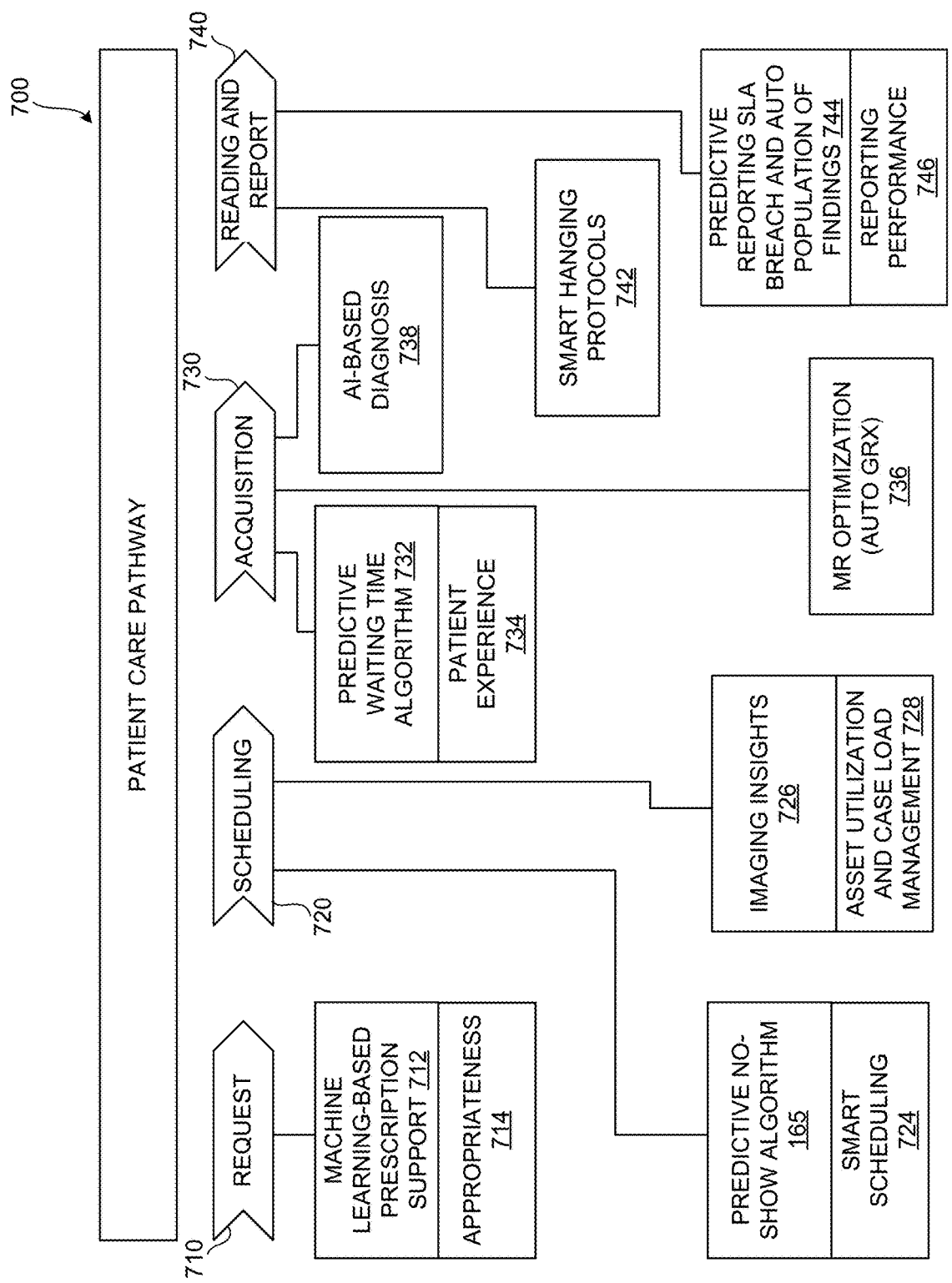
FIGS. 7-8 show example flow charts integrating artificial intelligence-driven prediction and modeling into an example patient care pathway.

FIG. 7 shows an example flow chart integrating AI-driven prediction and modeling into an example patient care pathway 700. At block 710, a request is generated. Machine learning-based prescription support 712 can be provided with an exam request, scheduling request, prescription request, etc., as determined (e.g., using an AI model, etc.) to be appropriate 714 to a given context (e.g., user context, application context, healthcare context, etc.). Appropriateness 714 can be evaluated using an AI model to correlate patient characteristics, symptoms, etc., to prescription information to treat the symptoms for the particular patient composition, for example.

At block 720, scheduling is performed. For example, a predictive no-show algorithm model 165 can be leveraged by a smart scheduler 724 to provide smart scheduling and reduce missed appointments, underutilized resources, delayed patient care, etc. For example, a predicted likelihood of patient no-shows at a location for a time period can be used by the smart scheduler 724 to dynamically adjust or generate a schedule for the time period accounting for likely/unlikely no-shows. Such a schedule can include one or more patients pre-scheduled to fill in for one or more patients missing appointments, one or more patients on standby to fill missing appointment(s) on short notice (e.g., based on likelihood of availability, distance from location, urgency, etc.), etc. At block 720, scheduling can also leverage imaging insights 726 such as a convolutional neural network-based image analysis, etc., to identify one or more objects of interest in an image and/or otherwise perform computer-aided diagnosis of the image data to uncover a likely diagnosis, further aspects to evaluate, etc., which can be automatically scheduled (or suggested to be scheduled) for the patient. Imaging insights 726 can be combined with asset utilization and case load management 728 to schedule patients, staff, and equipment to efficiently accommodate patient, staff, and equipment needs/requirements in an allotted period of time. For example, another AI model can process patients and exams/tests/procedures/etc. to be scheduled with respect to available personnel and equipment resources to provide those exams/tests/procedures/etc., combined with a likelihood of patient no-show and/or other analysis, and provide input to schedule appointments for the time period for the location.

At block 730, data acquisition is conducted. For example, acquisition can leverage a predictive wait time algorithm 732, imaging optimization 736 (e.g., MR optimization, etc.), AI-based computer-aided diagnosis (CAD) 738, etc., to acquire information regarding the patient. For example, the predictive wait time algorithm 732 can provide an indication of how long a patient will wait to be seen, how long an exam/test/procedure will take to be conducted, etc. Such predicted wait time information can be leveraged to provide an improved patient experience 734, for example. Image acquisition settings, etc., can be optimized 736 to improve image acquisition time, image quality, diagnostic analysis, etc., and an AI model can be applied to the resulting image data (e.g., a CNN, other deep learning neural network model, etc.) to predict and/or otherwise provide a diagnosis from the available image and/or other data for the patient, for example.

At block 740, reading and reporting can be provided using a smart hanging protocol 742 to arrange images, test results, exam data, patient history, and/or other information for clinician review. Predictive reporting 744 can provide an indication of a potential SLA breach, auto-populate findings for review and/or further processing, etc., for improved performance 746 in reporting, diagnosis, treatment, propagation of information for further processing, etc.

Figure 8:
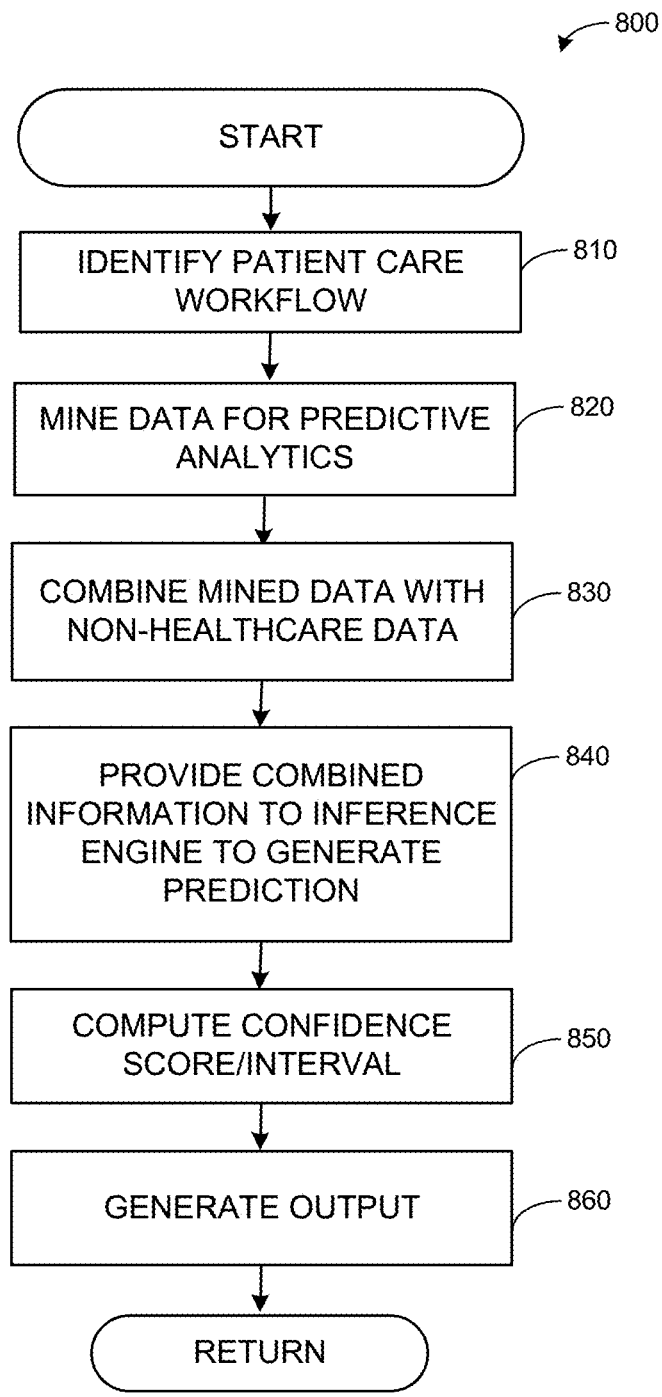

FIG. 8 provides an example illustration of the scheduling (e.g., block 720) of patient care including prediction of and reaction to patient no-shows. At block 810, a patient care workflow is identified (e.g., provided in an exam request/reason for exam, extracted from a patient record, identified in a departmental schedule, etc.). For example, a schedule of one or more patients to be seen by one or more healthcare practitioners at a hospital can be retrieved from a hospital information system 110. At block 820, data related to the identified patient and/or patient care workflow is mined for predictive analytics. For example, data 115 for the patient(s) on the schedule, healthcare practitioner(s) involved in the schedule, resource(s) involved in the schedule, etc., can be extracted from one or more systems 110 such as a HIS, RIS, CIS, CVIS, PACS, LIS, EMR, etc., and mined for predictive analysis. The data cube 120 can format the data 115, combine the data 115, and/or otherwise transform the data 115 to be processed by the inferencing engine 160, for example.

At block 830, mined data is combined with non-healthcare data such as appointment data, weather data, traffic data, resource information, etc. For example, the mined healthcare data 115 is enriched with weather data 150, traffic information relative to patient, provider, and/or other healthcare location, etc. Thus, the healthcare data can be enriched with non-healthcare data providing context, environment, conflicting schedule constraints, etc., that can affect predictive analysis of a future event such as a patient no-show for a scheduled appointment, etc.

At block 840, the combined information is provided to the machine learning inference engine 160 to generate a prediction regarding an outcome associated with the information (e.g., a likelihood or probability of a patient not showing up for an appointment, etc.). For example, a random forest model 165 can be used to represent schedule data, workflow data, patient information, weather and/or traffic projection(s), etc., using a plurality of decision trees. The decision trees can be constructed at training time using known or "ground truth" verified data. Upon deployment in the inference engine 160, the model(s) 165 can output a mode regression and/or mean classification of the decision trees representing a probability of patient no-show, for example.

At block 850, a confidence score and/or interval associated with the prediction is computed. For example, the model 165 may output a yes or no answer and/or a percentage probability that a patient under review will not attend his/her appointment (a no show). The confidence interval associated with the model determination can be formed, for example, by determining a mean probability of patient no show and a standard deviation from the mean over a plurality of determinations (e.g., taking a square root of squared differences in range of available determinations, etc.) and calculating a margin of error using the mean, standard deviation, a desire confidence level (e.g., 90%, 95%, 99%, etc.). The margin of error can be subtracted from the mean and added to the mean to determine your confidence interval around the calculated value from the model 165, for example.

At block 860, an output is generated. For example, a worklist with the prediction, confidence score, and a recommendation/adjustment to the schedule and/or other workflow element are generated and provided based on the combination of prediction and confidence score and/or interval. A result generated by the inference engine 160 and provided to the data access layer 140 via a REST command can be used to drive dashboard 130 output as well as provide output to a scheduler associated with one or more information systems 110 to adjust equipment, personnel, patient, and/or other resource allocation based on integrated workflow prediction(s) 170, for example. Output can be used to help ensure compliance with service level agreement(s) (SLA), reduce and/or maintain patient wait time, and trigger a reminder and/or other preventative or remedial action for one or more patients when the inference engine 160 indicates a high likelihood of patient no-show. Such action, triggered by the engine output 130, 170, etc., can improve resource utilization, patient care, and system responsiveness, for example.

FIGS. 9-14 depict example interfaces generated by the example systems and methods of FIGS. 1-8. For example, FIG. 9 shows an example predictive no-show interface 900. The example interface 900 illustrates predictive patient no-show for radiology examinations based on machine learning from the inference engine 160, for example. For each scheduled patient, a tile 910-912 representing the patient and their appointment is shown in conjunction with weather forecast information 920-922 for their appointment. Alternatively or in addition to weather forecast information, traffic information, etc., can be provided via the example interface 900 in conjunction with the patient 910-912 and prediction 930-932 information. A probability of no-show 930-932 is displayed on the interface 900, and a rescheduling option 940 is presented when the patient has a high probability of missing the scheduled appointment (e.g., >50%, etc.).

FIG. 10 shows an example dashboard 1000 listing a set of patients and their information, scheduled appointment information, predicted probability of no-show, etc. A user can interact with the example dashboard 1000 to evaluate a schedule or workflow and patients included in that schedule/workflow/worklist. In certain examples, a user can select a patient's no-show probability to view additional information that lead to the generation of the corresponding probability. Selecting a patient and/or other person listed in the dashboard 1000 can retrieve contact information for the person and/or another person to contact them in the event of a no-show, in advance of a probable no-show, etc., to prompt the person to attend, to fill the spot with another person, etc. Via the example interface 1000, a daily schedule, weekly schedule, monthly schedule, etc., can be viewed and modified, for example. In certain examples, a schedule or worklist can be viewed by modality and/or other criterion via the example dashboard interface 1000. The example interface 1000 can provide predicted no-shows for a given modality for a next day's appointments for a user, department, etc., for example.

Figure 11:
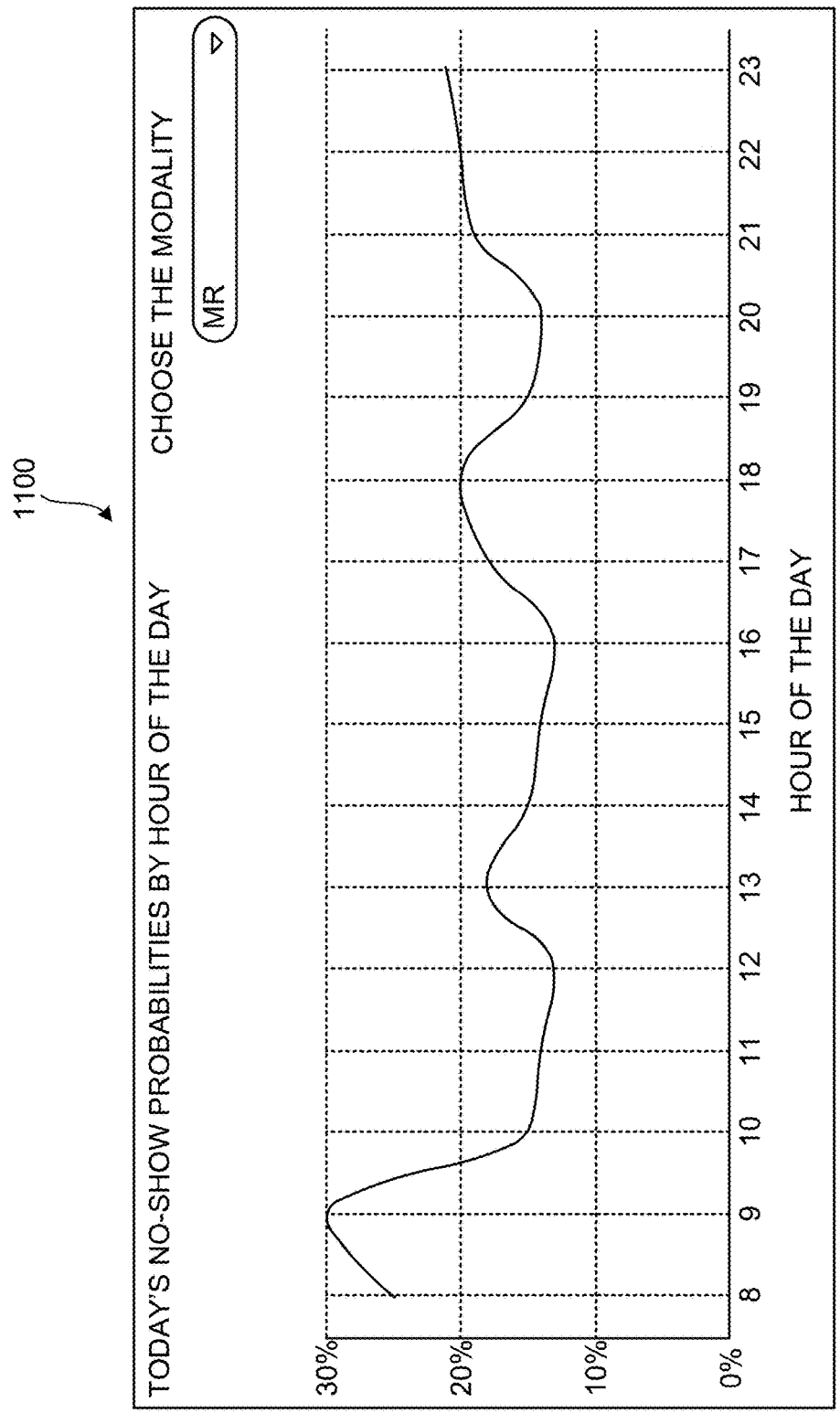

FIG. 11 shows an example graph 1100 of predicted no-show probabilities for each hour of a day. Thus, for a particular modality (e.g., x-ray, ultrasound, MR, etc.), a probability of patient no-show can vary by hour throughout the day. The example graph 1100 conveys the probabilities to a user, for example. Using the example graph 1100, a user can view attendance prediction(s) and plan for demand, strategize to increase demand, etc. In certain examples, the graph 1100 is connected to the dashboard 1000 to allow a user to view a wait list and/or contact information to try and fill empty schedule slots, help ensure a person shows for an appointment, etc.

Figure 12:
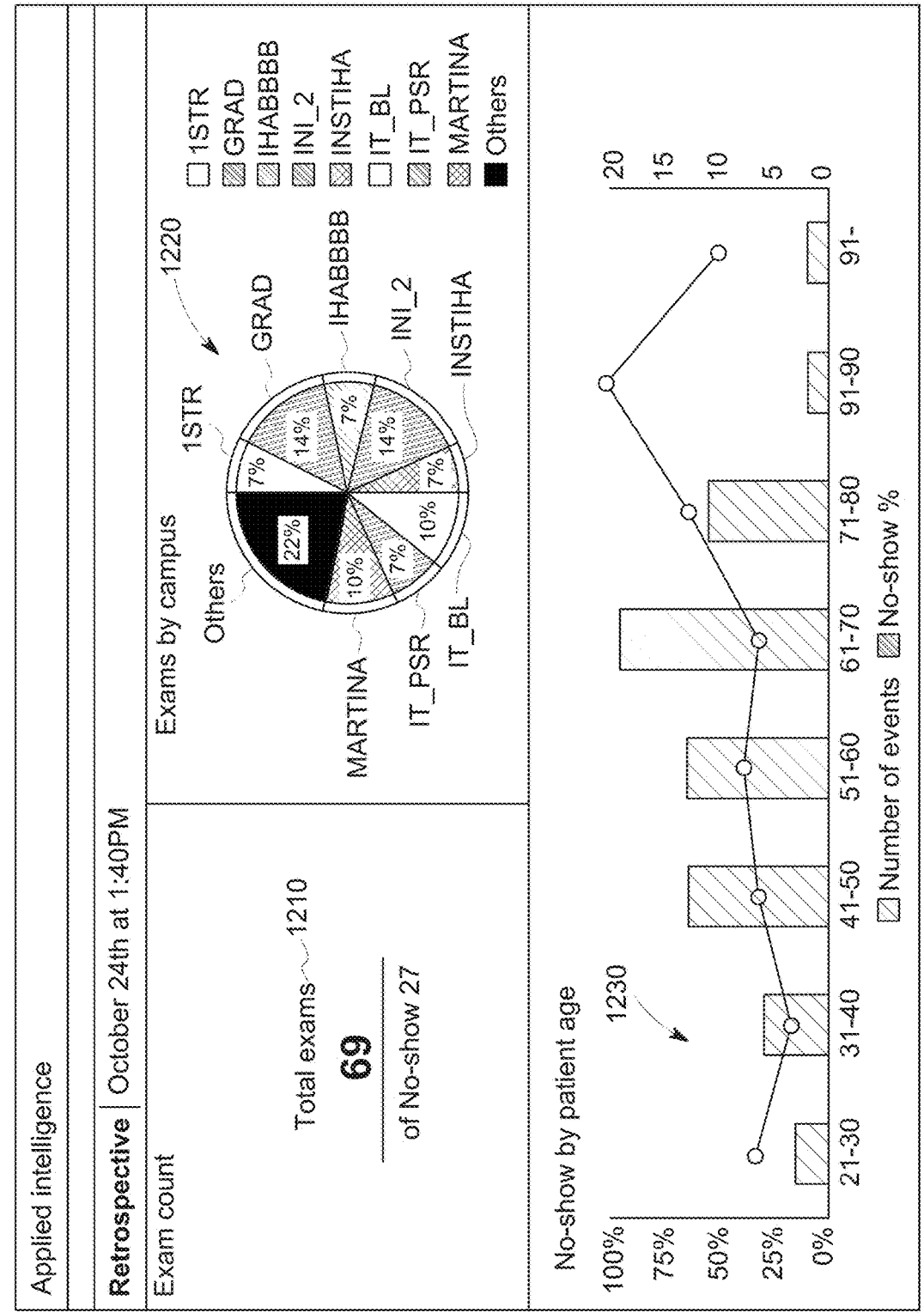
Figure 13:
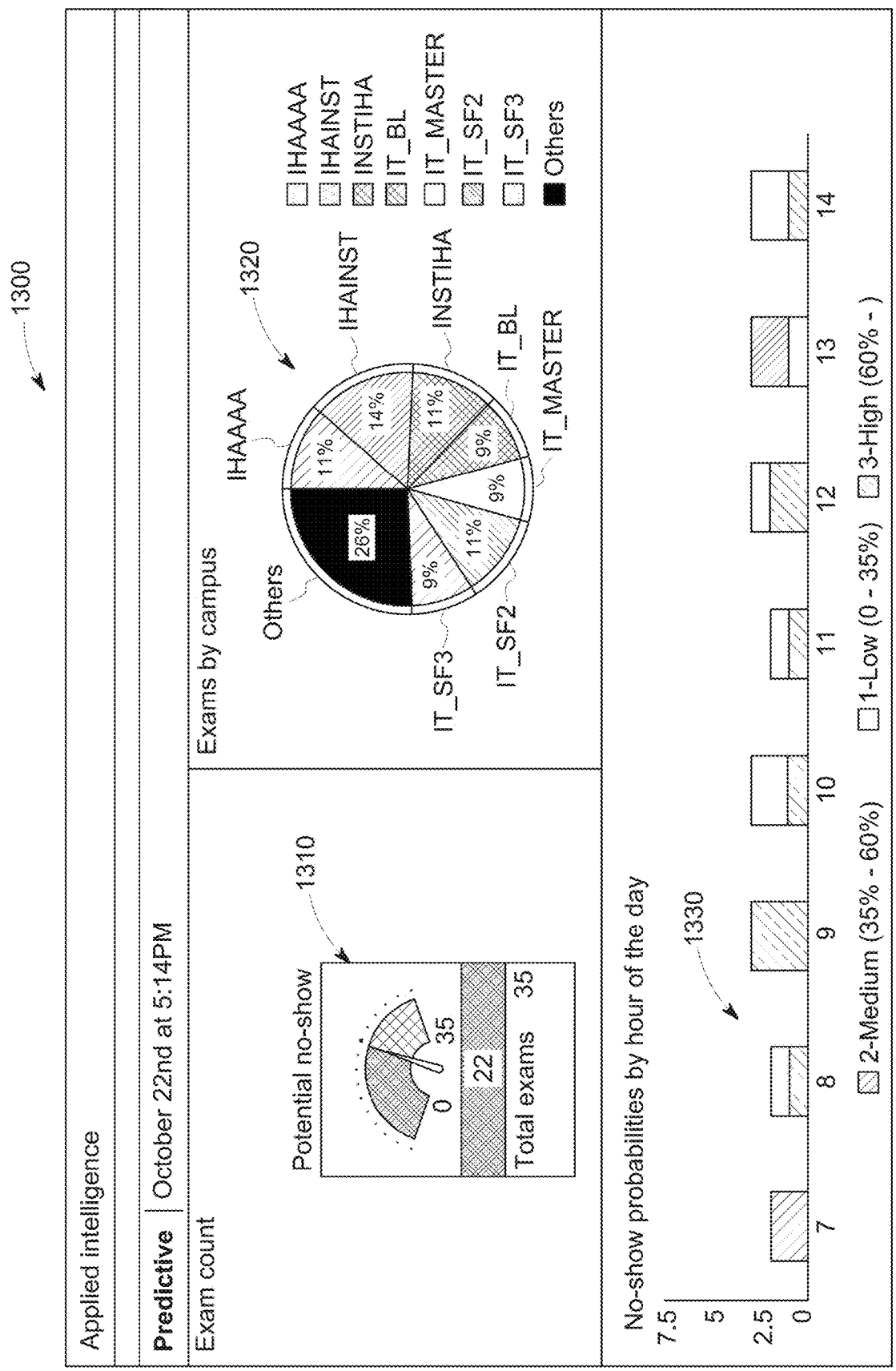

FIG. 12 illustrates an example retrospective dashboard 1200 providing a historical recap or look back at actual no-shows for patient appointments. As shown in the example of FIG. 12, out of a total number of exams for a given day and/or other time period, a number and/or percentage of patient no-shows can be calculated and displayed 1210. Exams and/or other appointments can be broken down by location (e.g., department, facility, etc.), type, and/or other criterion 1220. Additionally, no-shows can be broken down by patient-type, patient age, visit type, etc., to provide a number of events, a no-show percentage, etc. 1230. Elements of the interface 1200 can be selected and/or otherwise interacted with to retrieve patient records, trigger comparative analysis (e.g., between time periods, locations, event types, patients, etc.), FIG. 13 illustrates an example predictive dashboard 1300 providing a prediction of patient no-shows for a particular location, appointment type, etc. For example, the interface 1300 can provide a number and/or percentage of likely no-shows out of a total number of appointments for a location (e.g., facility, department, etc.), a time period, an exam type, etc. 1310. The example dashboard 1300 can break down exams by location (e.g., facility, department, etc.), type, etc. 1320. Additionally, a no-show probability can be calculated and displayed by time, location, etc. 1330. As shown in the example of FIG. 13, the determined patient no-show probability can be categorized into probability levels such as low (e.g., 0-35%), medium (e.g., 35-60%), and high (e.g., 60%+). Probability levels can be used to drive schedule adjustment, notification, etc.

FIG. 14 shows an example random forest output 1400 processing attendance data collected over a period of time (e.g., one year, two years, three years, etc.). In the example of FIG. 14, a confusion matrix can be generated for monitored patient shows and no-shows such as used in training of the machine learning model for no-show prediction. In the example of FIG. 14, a random forest trained and deployed at a healthcare facility is analyzed to identify a number of correctly identified shows, a number of correctly identified no-shows, a number of missed shows, and a number of false positive no-shows to generate predictions at a 90.8% precision with an 82.6% recall from false negatives.

Flowcharts representative of example machine readable instructions for implementing and/or executing in conjunction with the example systems, algorithms, and interfaces of FIGS. 1-6 and 9-14 are shown in FIGS. 7-8. In these examples, the machine readable instructions comprise a program for execution by a processor such as the processor 1512 shown in the example processor platform 1500 discussed below in connection with FIG. 15. The program can be embodied in software stored on a tangible computer readable storage medium such as a CD-ROM, a floppy disk, a hard drive, a digital versatile disk (DVD), a BLU-RAY™ disk, or a memory associated with the processor 1512, but the entire program and/or parts thereof could alternatively be executed by a device other than the processor 1512 and/or embodied in firmware or dedicated hardware. Further, although the example program is described with reference to the flowchart and/or process(es) illustrated in FIGS. 7-8, many other methods of implementing the examples disclosed and described here can alternatively be used. For example, the order of execution of the blocks can be changed, and/or some of the blocks described can be changed, eliminated, or combined.

As mentioned above, the example process(es) of FIGS. 7-8 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process(es) of FIGS. 7-8 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

The subject matter of this description may be implemented as stand-alone system or for execution as an application capable of execution by one or more computing devices. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

Memory and processor as referred to herein can be stand-alone or integrally constructed as part of various programmable devices, including for example a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like or as part of a Computing Device, and any combination thereof operable to execute the instructions associated with implementing the method of the subject matter described herein.

Computing device as referenced herein can include: a mobile telephone; a computer such as a desktop or laptop type; a Personal Digital Assistant (PDA) or mobile phone; a notebook, tablet or other mobile computing device; or the like and any combination thereof.

Computer readable storage medium or computer program product as referenced herein is tangible (and alternatively as non-transitory, defined above) and can include volatile and non-volatile, removable and non-removable media for storage of electronic-formatted information such as computer readable program instructions or modules of instructions, data, etc. that may be stand-alone or as part of a computing device. Examples of computer readable storage medium or computer program products can include, but are not limited to, RAM, ROM, EEPROM, Flash memory, CD-ROM, DVD-ROM or other optical storage, magnetic cassettes, magnetic tape, magnetic disk storage or other magnetic storage devices, or any other medium which can be used to store the desired electronic format of information and which can be accessed by the processor or at least a portion of the computing device.

The terms module and component as referenced herein generally represent program code or instructions that causes specified tasks when executed on a processor. The program code can be stored in one or more computer readable mediums.

Network as referenced herein can include, but is not limited to, a wide area network (WAN); a local area network (LAN); the Internet; wired or wireless (e.g., optical, Bluetooth, radio frequency (RF)) network; a cloud-based computing infrastructure of computers, routers, servers, gateways, etc.; or any combination thereof associated therewith that allows the system or portion thereof to communicate with one or more computing devices.

The term user and/or the plural form of this term is used to generally refer to those persons capable of accessing, using, or benefiting from the present disclosure.

Figure 15:
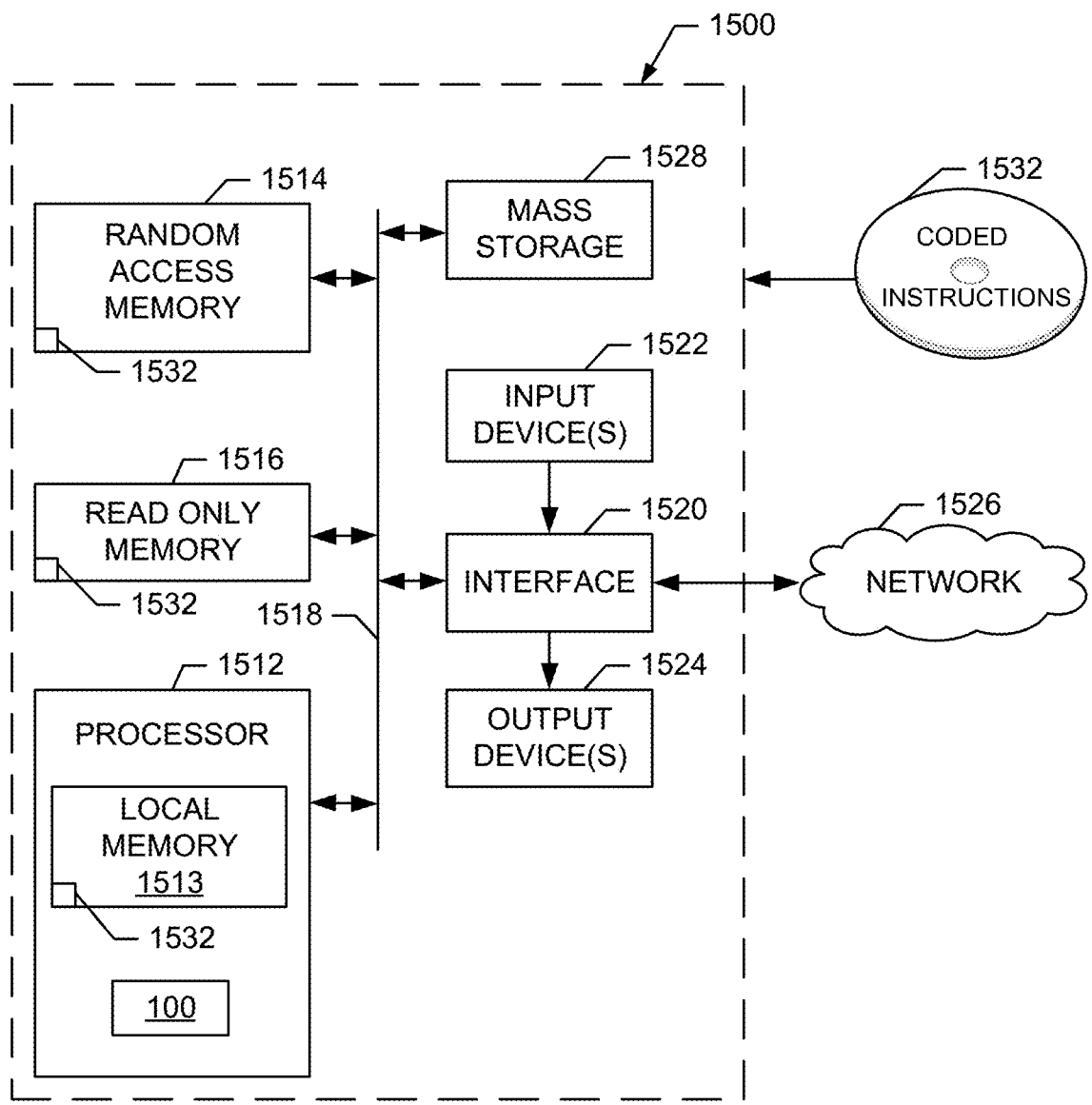
FIG. 15 is a block diagram of an example processor platform capable of executing instructions to implement the example systems and methods disclosed and described herein.

FIG. 15 is a block diagram of an example processor platform 1500 capable of executing instructions to implement the example systems and methods disclosed and described herein. The processor platform 1500 can be, for example, a server, a personal computer, a mobile device (e.g., a cell phone, a smart phone, a tablet such as an IPAD™), a personal digital assistant (PDA), an Internet appliance, or any other type of computing device.

The processor platform 1500 of the illustrated example includes a processor 1512. The processor 1512 of the illustrated example is hardware. For example, the processor 1512 can be implemented by one or more integrated circuits, logic circuits, microprocessors or controllers from any desired family or manufacturer.

The processor 1512 of the illustrated example includes a local memory 1513 (e.g., a cache). The processor 1512 of the illustrated example is in communication with a main memory including a volatile memory 1514 and a non-volatile memory 1516 via a bus 1518. The volatile memory 1514 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1516 can be implemented by flash memory and/or any other desired type of memory device. Access to the main memory 1514, 1516 is controlled by a memory controller.

The processor platform 1500 of the illustrated example also includes an interface circuit 1520. The interface circuit 1520 can be implemented by any type of interface standard, such as an Ethernet interface, a universal serial bus (USB), and/or a PCI express interface.

In the illustrated example, one or more input devices 1522 are connected to the interface circuit 1520. The input device(s) 1522 permit(s) a user to enter data and commands into the processor 1512. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1524 are also connected to the interface circuit 1520 of the illustrated example. The output devices 1524 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 1520 of the illustrated example, thus, typically includes a graphics driver card, a graphics driver chip or a graphics driver processor.

The interface circuit 1520 of the illustrated example also includes a communication device such as a transmitter, a receiver, a transceiver, a modem and/or network interface card to facilitate exchange of data with external machines (e.g., computing devices of any kind) via a network 1526 (e.g., an Ethernet connection, a digital subscriber line (DSL), a telephone line, coaxial cable, a cellular telephone system, etc.).

The processor platform 1500 of the illustrated example also includes one or more mass storage devices 1528 for storing software and/or data. Examples of such mass storage devices 1528 include floppy disk drives, hard drive disks, compact disk drives, Blu-ray disk drives, RAID systems, and digital versatile disk (DVD) drives.

The coded instructions 1532 can be stored in the mass storage device 1528, in the volatile memory 1514, in the non-volatile memory 1516, and/or on a removable tangible computer readable storage medium such as a CD or DVD. The instructions 1532 can be executed by the processor 1512 to implement the example system 100, 400, etc., as disclosed and described above.

From the foregoing, it will be appreciated that example methods, apparatus and articles of manufacture have been disclosed that improve processing of data and associated documents. The disclosed methods, apparatus and articles of manufacture improve the efficiency of using a computing device and an interface being driven by the computing device by providing relevant documents in the context of a particular patient and exam order for display and interaction via a single interface. In certain examples, access to the larger set of documents is also maintained. Certain examples improve a computer system and its process and user interface display through the ability to apply filters in a manner previously unavailable. While prior approaches did not provide such matching and filtering and suffered from lack of granularity which results in loss of relevant data, computing performance issues, impact on patient safety, etc., certain examples alter the operation of the computing device and provide a new interface and document interaction. The disclosed methods, apparatus and articles of manufacture are accordingly directed to one or more improvement(s) in the functioning of a computer, as well as a new matching methodology and user interface layout, structure, and interaction for patient and exam information.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A predictive workflow analytics apparatus comprising:
a memory including instructions; and
at least one processor to execute the instructions to at least:
orchestrate, using an orchestration service, a combination of non-healthcare information with healthcare workflow data including patient information and a scheduled appointment for the patient;
generate a prediction including a probability of a patient no-show to the scheduled appointment using an artificial intelligence engine in an inferencing mode, the artificial intelligence engine including a trained patient no-show model selected from a plurality of models in the artificial intelligence engine to predict the probability of the patient no-show based on the combination of healthcare workflow data and non-healthcare information from the orchestration service;
synchronize the prediction and a schedule including the scheduled appointment for the patient; and
generate an interactive dashboard including the synchronized prediction and the schedule and at least one of: a) a first option to adjust the schedule to replace the patient based on the probability of the patient no-show, b) a second option to adjust the schedule to move the patient to a different time based on the probability of the patient no-show.

2. The apparatus of claim 1, wherein the non-healthcare data includes at least one of weather forecast data, traffic forecast data, or holiday information.

3. The apparatus of claim 1, wherein the patient no-show model is to be implemented using at least one of a random forest model or a neural network model.

4. The apparatus of claim 1, wherein the at least one processor is to operate the artificial intelligence engine in a training mode to train the patient no-show model.

5. The apparatus of claim 4, wherein patient no-show prediction accuracy feedback provided in the inferencing mode is to trigger the at least one processor to enter the training mode.

6. The apparatus of claim 1, wherein the at least one processor is to synchronize the prediction and the schedule using a data cube.

7. The apparatus of claim 1, wherein the interactive dashboard is to include a third option to send a reminder of the scheduled appointment to the patient.

8. The apparatus of claim 1, wherein the at least one processor is to retrieve the healthcare workflow data using a fast healthcare interoperability resources application programming interface that defines the resources as a set of at least one of operations or interactions to retrieve the healthcare workflow data based on type.

9. The apparatus of claim 8, wherein the at least one processor is to interface with a scheduling system to provide the schedule, the prediction, and a selected one of the first option or the second option to the scheduling system via the fast healthcare interoperability resources application programming interface.

10. The apparatus of claim 1, wherein the interactive dashboard includes a predictive interface view and a retrospective interface view.

11. At least one non-transitory computer-readable storage medium comprising instructions which, when executed by at least one processor, cause the at least one processor to at least:
orchestrate, using an orchestration service, a combination of non-healthcare information with healthcare workflow data including patient information and a scheduled appointment for the patient;
generate a prediction including a probability of a patient no-show to the scheduled appointment using an artificial intelligence engine in an inferencing mode, the artificial intelligence engine including a trained patient no-show model selected from a plurality of models in the artificial intelligence engine to predict the probability of the patient no-show based on the combination of healthcare workflow data and non-healthcare information from the orchestration service;
synchronize the prediction and a schedule including the scheduled appointment for the patient; and
generate an interactive dashboard including the synchronized prediction and the schedule and at least one of: a) a first option to adjust the schedule to replace the patient based on the probability of the patient no-show, b) a second option to adjust the schedule to move the patient to a different time based on the probability of the patient no-show.

12. The at least one computer-readable storage medium of claim 11, wherein the non-healthcare data includes at least one of weather forecast data, traffic forecast data, or holiday information.

13. The at least one computer-readable storage medium of claim 11, wherein the instructions, when executed, cause the at least one processor to operate the artificial intelligence engine in a training mode to train the patient no-show model.

14. The at least one computer-readable storage medium of claim 13, wherein patient no-show prediction accuracy feedback provided in the inferencing mode is to trigger the at least one processor to enter the training mode.

15. The at least one computer-readable storage medium of claim 11, wherein the interactive dashboard is to include a third option to send a reminder of the scheduled appointment to the patient.

16. The at least one computer-readable storage medium of claim 11, wherein the at least one processor is to retrieve the healthcare workflow data using a fast healthcare interoperability resources application programming interface that defines the resources as a set of at least one of operations or interactions to retrieve the healthcare workflow data based on type.

17. The at least one computer-readable storage medium of claim 16, wherein the instructions, when executed, cause the at least one processor to interface with a scheduling system to provide the schedule, the prediction, and a selected one of the first option or the second option to the scheduling system via the fast healthcare interoperability resources application programming interface.

18. A method to apply predictive analytics to drive a patient care pathway, the method comprising:
orchestrating, using an orchestration service, a combination of non-healthcare information with healthcare workflow data including patient information and a scheduled appointment for the patient;
generating a prediction including a probability of a patient no-show to the scheduled appointment using an artificial intelligence engine in an inferencing mode, the artificial intelligence engine including a trained patient no-show model selected from a plurality of models in the artificial intelligence engine to predict the probability of the patient no-show based on the combination of healthcare workflow data and non-healthcare information from the orchestration service;
synchronizing the prediction and a schedule including the scheduled appointment for the patient; and
generating an interactive dashboard including the synchronized prediction and the schedule and at least one of: a) a first option to adjust the schedule to replace the patient based on the probability of the patient no-show, b) a second option to adjust the schedule to move the patient to a different time based on the probability of the patient no-show.

19. The method of claim 18, wherein the non-healthcare data includes at least one of weather forecast data, traffic forecast data, or holiday information.

20. The method of claim 18, further including, triggering, based on patient no-show prediction accuracy feedback, a training mode to retrain the patient no-show model.

* * * * *